United States Patent [19]  [11] Patent Number: 4,936,542
Beard, deceased  [45] Date of Patent: Jun. 26, 1990

[54] CATHETER FLOW CONTROL VALVE

[75] Inventor: Robert W. Beard, deceased, late of Placerville, Calif., by Wanda S. Beard, executrix

[73] Assignee: Abbott Laboratories, Abbott Park, Ill.

[21] Appl. No.: 328,253

[22] Filed: Mar. 27, 1989

[51] Int. Cl.⁵ .................... F16K 7/12; A61M 39/00
[52] U.S. Cl. .................................. 251/117; 251/331; 604/34; 604/250
[58] Field of Search .................. 251/117, 331; 604/34, 604/250

[56] References Cited

U.S. PATENT DOCUMENTS

| 3,104,825 | 9/1963 | Hayes | 239/407 |
|---|---|---|---|
| 3,675,891 | 7/1972 | Reynolds et al. | 251/117 |
| 4,011,893 | 3/1977 | Bentley | 138/43 |
| 4,079,737 | 3/1978 | Miller | 128/214 R |
| 4,192,303 | 3/1980 | Young et al. | 128/214 R |
| 4,245,636 | 1/1981 | Sparks et al. | 128/214 R |
| 4,267,835 | 5/1981 | Barger et al. | 128/214 E |
| 4,278,083 | 7/1981 | Young et al. | 128/214 R |
| 4,291,702 | 9/1981 | Cole et al. | 128/675 |
| 4,300,552 | 11/1981 | Cannon | 604/250 X |
| 4,300,571 | 11/1981 | Waldbillig | 128/673 |
| 4,341,224 | 7/1982 | Stevens | 128/675 |
| 4,444,198 | 4/1984 | Petre | 128/673 |
| 4,457,487 | 7/1984 | Steigerwald | 251/117 |
| 4,501,300 | 2/1985 | Murphy | 138/46 |
| 4,509,946 | 4/1985 | McFarlane | 604/246 |
| 4,517,844 | 5/1985 | Powell | 73/707 |
| 4,537,387 | 8/1985 | Danby et al. | 251/331 |
| 4,550,748 | 11/1985 | Nunez | 137/605 |
| 4,552,336 | 11/1985 | Pastrone | 251/331 |
| 4,576,181 | 3/1986 | Wallace et al. | 128/675 |
| 4,624,662 | 11/1986 | Le | 604/249 |
| 4,638,811 | 1/1987 | Bisera et al. | 128/673 |
| 4,645,496 | 2/1987 | Oscarsson | 604/248 |
| 4,648,868 | 3/1987 | Hardwick et al. | 604/32 |
| 4,683,894 | 8/1987 | Kodama et al. | 128/675 |
| 4,696,305 | 9/1987 | von Berg | 128/673 |
| 4,703,759 | 11/1987 | Merrick et al. | 128/673 |
| 4,739,770 | 4/1988 | Stephens et al. | 128/675 |

FOREIGN PATENT DOCUMENTS

| 67458 | 12/1982 | European Pat. Off. . | |
|---|---|---|---|
| 2939464 | 4/1980 | Fed. Rep. of Germany | 251/117 |
| 160807 | 11/1985 | Fed. Rep. of Germany . | |
| 1360439 | 7/1974 | United Kingdom . | |

Primary Examiner—Arnold Rosenthal
Attorney, Agent, or Firm—Christensen, O'Connor, Johnson & Kindness

[57] ABSTRACT

A valve for selectively controlling flow within a fluid line between a relatively low capillary flow rate and a flushing flow. A flush valve (10) comprises a base (14) and a cover (16) that secures an elastomeric membrane (18) in place over a flow path (32) formed in the base. The flow path includes an inlet passage (34) connected in fluid communication to an outlet passage (50) by a capillary groove (38). The membrane seals over the capillary groove to define a capillary passage (48), which restricts fluid flow through the flush valve to the capillary flow rate. A user may selectively enable the relatively greater fluid flow through the device by deforming the membrane away from the capillary groove, thereby creating a relatively larger flushing flow passage (66). The flushing flow of fluid through the region of the capillary groove serves to carry away any obstruction that may be present in the groove or downstream of the flush valve.

23 Claims, 2 Drawing Sheets

CATHETER FLOW CONTROL VALVE

TECHNICAL FIELD

The present invention relates to an apparatus for controlling flow in a fluid line, and more particularly, to a valve that normally restricts flow through a capillary channel, but which can selectively provide a substantially greater flushing flow.

BACKGROUND OF THE INVENTION

Catheters connected to inject a medicinal fluid into a patient's cardiovascular system are subject to occlusion as blood clots or thrombi form within the catheter passage. To minimize the occurrence of this problem, a very low flow rate of the fluid is continuously maintained through the catheter from a source container. Periodically, medical personnel must momentarily ope a valve to create a substantially greater flow rate of fluid to flush incipient thrombi from the catheter. In addition, this flushing flow of fluid may be momentarily enabled prior to connection of the catheter to the patient, in order to evacuate air from the line and fill it with the fluid. In the medical field, a device used to restrict fluid flow and selectively provide a flushing flow through a catheter is known as "flush valve." A typical flush valve contains a very small diameter capillary flow passage that limits fluid flow to the desired low rate. Typically, the relatively greater flushing flow is effected in such devices by opening a separate parallel path that does not include the restriction of the capillary flow passage.

Exemplary of prior art flush valves is the design disclosed in U.S. Pat. No. 4,192,303. In this flush valve, a flexible conduit defines a passage between an inlet and an outlet. Positioned coaxially in the flexible conduit is a cylindrical plug member that has a raised band intermediate its ends. The diameter of the raised band is sufficient to seal against the inner surface of the flexible conduit, normally limiting fluid flow through a marine bore formed through the longitudinal center of the plug. To produce the larger flushing flow, a user squeezes the flexible conduit, causing a passage to open between the raised band and the inner surface of the conduit. Fluid then flows through the larger passage, bypassing the flow retriction normally imposed by the marine bore. When released, the flexible conduit reseals against the raised band, closing the bypass passage and shutting off flow of fluid through it. Any obstruction in the marine bore capillary flow passage is not cleared by the flushing flow in such prior art flush valves, because the flushing flow is completely separate from the capillary flow passage. Consequently, obstruction of the marine bore may eventually allow thrombi to block the catheter downstream of the flush valve.

SUMMARY OF THE INVENTION

In accordance with the present invention, apparatus are provided for controlling flow in a fluid line. The apparatus include a base having an upper surface, and an inlet port and an outlet port that are adapted to connect to the fluid line. Formed in the upper surface of the base are an inlet channel and an outlet channel that are respectively connected in fluid communication with the inlet port and the outlet port. In addition, the upper surface includes a capillary groove that provides fluid communication between the inlet and outlet channels. A flexible membrane substantially overlaps the upper surface of the base and is resiliently deformable between a capillary configuration and a flushing configuration. Means are provided to seal the membrane against the upper surface of the base, defining a capillary passage between the capillary groove and the membrane. Further included in the apparatus are means for selectively deforming the membrane from its capillary configuration, in which the membrane seals against the capillary groove to permit fluid flow only through the capillary passage, into its flushing configuration, in which the membrane is distorted away from the capillary groove. In the flushing configuration, the capillary passage is enlarged to create a flushing flow passage between the membrane and the upper surface of the base, which permits greatly increased fluid flow through the apparatus and fluid line.

The means for sealing the membrane may include a cover having a lower and an upper surface. The cover is securable to the base with the membrane disposed between the upper surface of the base and the lower surface of the cover. A flow control aperture is provided in the cover, disposed about the capillary groove. Extending from the upper surface of the base through the flow control aperture is a flow control projection. The flow control projection separates the inlet and outlet channels, and includes a sealing surface on which the capillary groove is formed, covered by the membrane. The means for selectively deforming the membrane comprise a grip that is secured to the membrane. By grasping the grip, a user may distort the membrane away from the sealing surface of the flow control projection opening the flushing flow passage.

DESCRIPTION OF THE PREFERRED EMBODIMENT

Figure 1:
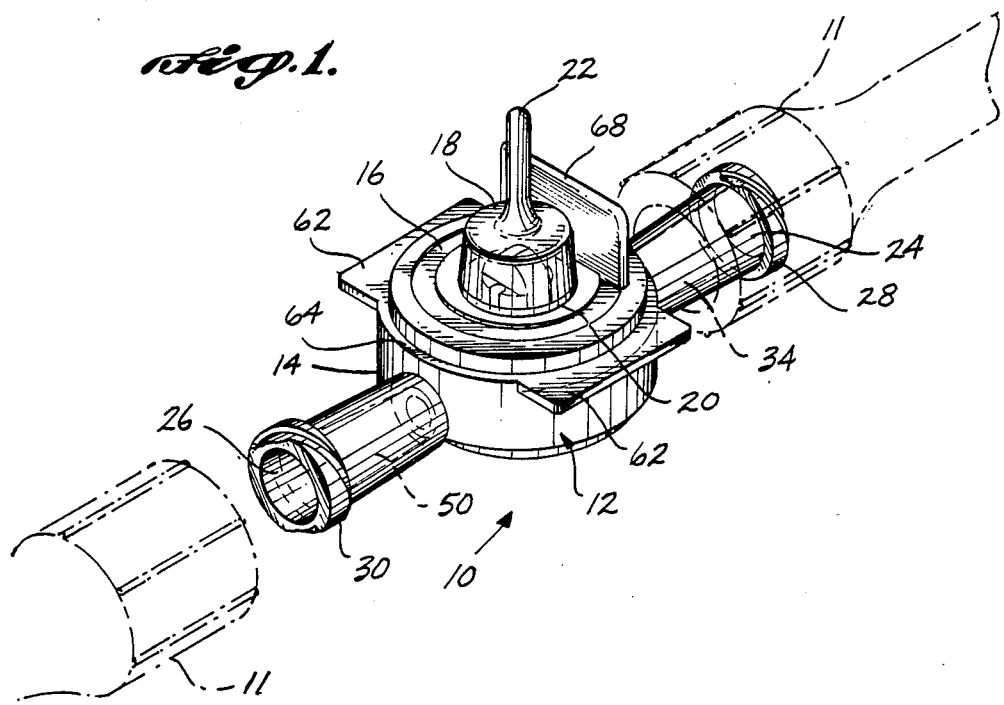
FIG. 1 illustrates the flush valve in an isometric view, showing the catheter line to which it is normally connected in phantom view.

The preferred embodiment of a flush valve 10 is shown in FIG. 1. Although not a part of the present invention, a catheter 11 is shown in phantom view in this figure, illustrating a typical application of flush valve 10 to control fluid flow from a reservoir (not shown) into the cardiovascular system of a patient. Flush valve 10 includes a housing 12 having a base 14 and a cover 16. Cover 16 captures a membrane 18 in place in overlying relationship to base 14, and seals the perimeter of the membrane to the base, as described below. A portion of membrane 18 extends through an aperture 20 formed in the cover, terminating in a grip 22 that provides means for actuating a flushing flow through flush valve 10. Base 14 and cover 16 preferably comprise a tough, rigid plastic such as polycarbonate, although other suitable materials such as nylon or stainless steel could be used. Membrane 18 is preferably formed of a resilient, elastomeric material such as silicon rubber.

An inlet port 24 and an outlet port 26 extend from opposite ends of base 14, although the distinction between "inlet" and "outlet" is somewhat meaningless, since flush valve 10 can be connected to control fluid flow through catheter 11 in either direction. Luer fittings 28 and 30 are respectively provided on inlet port 24 and on outlet port 26, adapting the inlet and outlet ports for connection to matching fittings on catheter 11. Alternatively, other types of suitable connectors may be provided on the inlet and outlet ports to adapt flush valve 10 for connection to catheter 11, as are well known in the art.

Figure 2:
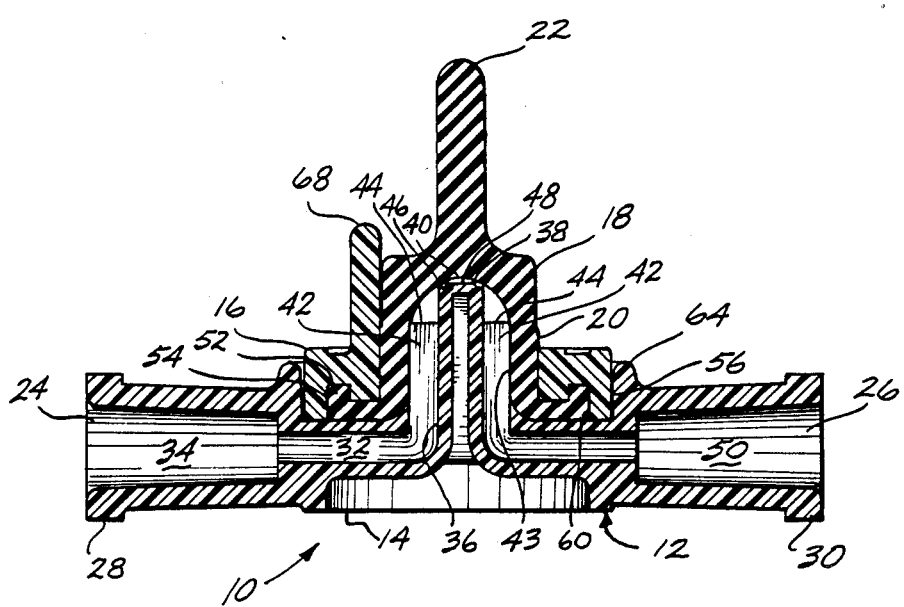
FIG. 2 shows an elevational, longitudinal cross section of the flush valve.
Figure 3:
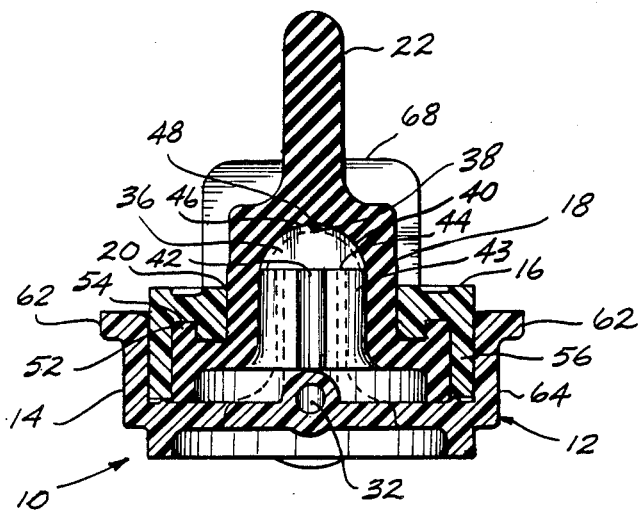
FIG. 3 shows an elevational transverse cross section of the flush valve.

Turning now to FIGS. 2 and 3, the internal construction of flush valve 10 is disclosed in two cross-sectional views, to better illustrate a flow path 32 that extends through the device. Flow path 32 comprises an inlet passage 34 that is formed in base 14 and which extends through inlet port 24, toward the center of the base, where a finger-like projection 36 protrudes upwardly from flow path 32. A V-shaped capillary groove 38 is formed in a convex upper portion 40 of projection 36. Capillary groove 38 connects fluid flow notches 42, which are formed on each side of a cylindrical lower portion 43 of the projection, in fluid communication with each other. Fluid flow notches 42 extend upwardly on each side of projection 36, toward recessed shoulders 44, which are disposed proxiamte its tip.

An inner surface 46 of membrane 18 seals against convex upper portion 40 of projection 36, at each side of capillary groove 38, thereby defining a capillary passage 48. The capillary flow configuration of membrane 18 is clearly illustrated in FIGS. 2 and 3. Fluid entering flush valve 10 through inlet passage 34 normally flows between fluid flow notches 42 at a very low rate, due to the restriction imposed by capillary passage 48. Downstream of capillary passage 48, the fluid flows into an outlet passage 50, which is also formed within base 14 and which extends through outlet port 26.

Peripheral sealing of membrane 18 between base 14 and cover 16 is insured by providing an upwardly extending flange 52 around the perimeter of the membrane, which fits into a mating groove 54 formed within the lower surface of cover 16. A lip 56 extends downwardly around the perimeter of cover 16 and is seated within base 14. Lip 56 is attached to base 14 by ultrasonically welding it in place; alternatively, the cover may be secured to the base with a suitable adhesive or mechanical fasteners. To further insure a hermetic seal between membrane 18 and base 14, flange 52 is slightly compressed as cover 16 is attached to base 14 so that an upper surfce 60 of the base inpinges into the adjacent suface of the membrane in a fluid tight seal.

Figure 4:
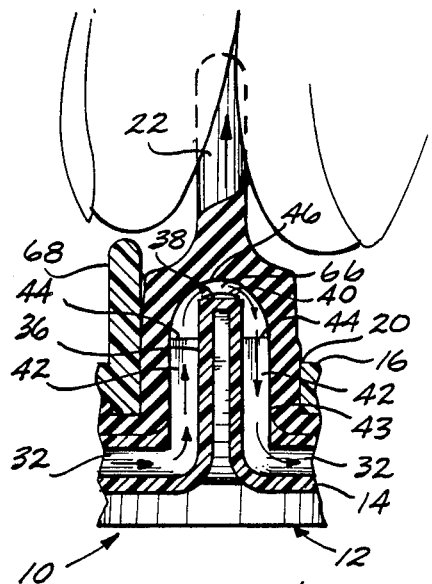
FIG. 4 is a breakaway cross-sectional view of the flush valve shown in the flushing configuration, as actuated by pulling upward on a grip.
Figure 5:
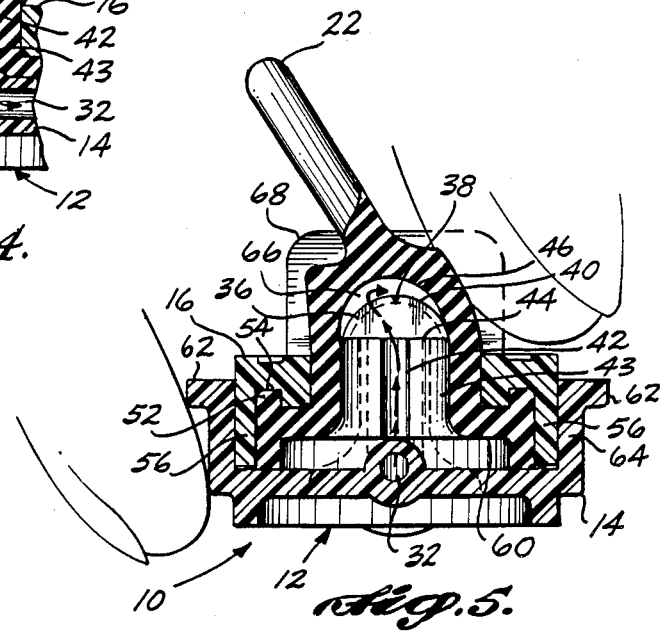
FIG. 5 is a breakaway cross-sectional view showing the flush valve in its flushing configuration, actuated by squeezing the grip and membrane towards one side of the device.

Two differnt methods for deforming membrane 18 to enable a flushing flow through flush valve 10 are illustrated in FIGS. 4 and 5. As shown in FIG. 4, the user may effect a flushing flow through the device by pulling upward on grip 22, breaking the seal between inner surface 46 of membrane 18 and convex upper portion 40 of projection 36 and creating a flushing flow passage 66 having a substantially larger cross-sectional area for fluid flow than is provided through capillary passage 48. Alternatively, as shown in FIG. 5, the portion of membrane 18 that extends through aperture 20 may be deflected to one side, also breaking the seal between inner surface 46 of membrane 18 and convex upper portion 40 of projection 36. Flanges 62 are provided on the upwardly projecting sides 64 of base 14 to enable a user to more conveniently deform membrane 18 to effect the flushing flow, by squeezing the exposed portion of membrane 18 and one of the flanges 62 between thumb and forefinger. Using either of these two techniques, fluid flow through flush valve 10, which is normally limited to the capillary flow rate through capillary passage 48, is substantially increased as flushing flow passage 66 is created by the deflection or deformation of membrane 18.

Any obstruction that may exist within capillary passage 48 is likely to be swept from capillary groove 38 by the flushing flow of fluid developed when the user deforms membrane 18 away from the tip of projection 36 to create flushing flow passage 66. In flush valve 10, both the capillary flow of fluid and the flushing flow fo fluid pass between inner surface 46 of membrane 18 and convex upper portion 40 of projection 36. Consequently, each time that a flushing flow rate is effected through flush valve 10, the entire flow path 32 is cleared of possible obstructions that might block capillary flow through flush valve 10.

An upward extending guard plate 68 is disposed next to the exposed portion of membrane 18 to prevent inadvertent deformation of the membrane, which might produce a flushing flow rate when inapporpriate. For example, accidental deformation of the membrane might be caused by a patient rolling onto flush valve 10. In its broadest scope, the present invention also encompasses several alternative configurations for connecting a membrane in sealing relationship to a capillary groove to define a capillary flow passage and for effecting flushing flow by distortion of the membrane away from the capillary groove to form a flushing flow passage. Instead of the membrane covering a capillary groove that is formed across an upwardly extending projection, the membrane could, for example, cover a capillary groove formed across a generally planar flow control surface, disposed on the upper surface of the base. As a further alternative, the flush valve might comprise a sealing membrane and a capillary groove recessed within a concave flow control channel formed within the base, with the membrane being deformed into the concave flow control channel to cover the capillary groove, thereby defining the capillary flow passage, using a spring biased tip. A plastic grip connected to the spring biased tip could be grasped and pulled to enlarge the passage, providing a flushing flow. These alternative embodiments are not illustrated; however, in view of the disclosure of the first preferred embodiment, the modifications to the illustrated preferred embodiment described above should be fully enabling to one of ordinary skill in the art.

While the present invention has been disclosed with respect to a preferred embodiment thereof and modifications thereto, those of ordinary skill in the art will understand that further modification may be made to the invention, including but not limited to those described above, within the scope of the claims that follow. Accordingly, it is intended that the scope of the invention not be limited to the disclosed preferred embodiment and modifications thereto, but instead be determined entirely by reference to the following claims and equivalents thereof.

The embodiments of the invention in which an exclusive property or privilege is claimed are defined as follows:

1. Apparatus for controlling fluid flow in a fluid line, said apparatus comprising:
   (a) a base having an upper surface, an inlet port, and an outlet port, said inlet and outlet ports being adapted to connect to the fluid line, said upper surface including an inlet channel and an outlet channel formed therein, said inlet channel being in fluid communication with the inlet port and said outlet channel being in fluid communication with the outlet port, said upper surface further including a capillary groove in a substantially non-planar portion of the base, in fluid communication with the inlet channel and the outlet channel;
   (b) a flexible membrane substantially overlapping the upper surface of the base, said membrane being curved to generally conform to the non-planar portion of the base in which the capillary groove is formed and being resiliently deformable between a capillary configuration and a flushing configuration;
   (c) means for sealing said membrane to the upper surface of the base, defining a capillary passage between the capillary groove and the membrane; and
   (d) means for selectively deforming the membrane from its capillary configuration, in which the membrane seals against the capillary groove to permit fluid flow only through the capillary passage, into its flushing configuration, in which the membrane is distorted away from the capillary groove, enlarging the capillary passage to define a flushing flow passage between the membrane and the upper surface of the base, permitting greatly increased flow through the apparatus and fluid line.

2. The apparatus of claim 1, wherein said means for sealing the membrane comprise a cover having a lower surface and an upper surface, said cover being secured to the base, said membrane being disposed between the lower surface of the cover and the upper surface of the base, said cover including a flow control aperture disposed about the capillary groove.

3. The apparatus of claim 2, wherein the non-planar portion of said base comprises a flow control projection extending from the upper surface of the base and through the flow control aperture, said flow control projection separating the inlet channel and the outlet channel, said flow control projection having a sealing surface across which the capillary groove is formed, covered by the membrane.

4. The apparatus of claim 3, wherein said means for selectively deforming the membrane comprise a grip secured to the membrane, said grip being grasped or deflected by a user to distort the membrane away from the sealing surface of the flow control projection in order to create the flushing flow.

5. The apparatus of claim 2, wherein the membrane includes flange means disposed around the flow control aperture, for sealingly attaching the membrane to the base when the cover is secured to the base.

6. The apparatus of claim 2, wherein the cover further comprises an outwardly projecting guard disposed adjacent the flow control aperture, said guard being operative to prevent unintended deformation of the membrane into its flushing configuration, by protecting the membrane from inadvertent contact with other objects in the environment.

7. Apparatus for selectively enabling either a capillary flow rate or a substantially greater flushing flow rate in a fluid line, comprising:
   (a) means for defining a fluid flow path through the apparatus between an inlet port and an outlet port, at least a portion of said fluid flow path being substantially curved and including a capillary groove that is open along one side;
   (b) membrane means that are curved to conform to the curved portion of the fluid flow path, for sealing closing the open side of said capillary groove to form a capillary passage, said capillary passage being operative to restrict fluid flow between the inlet port and the outlet port to the capillary flow rate; and
   (c) means for selectively distorting the membrane means away from the capillary groove, enlarging that portion of the fluid flow path, thus enabling the greater flushing flow rate of fluid through the fluid flow path, said flushing flow of fluid passing between the membrane means and the capillary groove.

8. The apparatus of claim 7, further comprising means for securing the membrane means to the means for defining the fluid flow path.

9. The apparatus of claim 7, wherein the means for defining a flow path comprise a rigid base and the curved portion of the fluid flow path comprises a projection extending outwardly from a surface of the base, said projection being disposed between the inlet port and the outlet port and having a tip on which the capillary groove is formed.

10. The apparatus of claim 9, wherein a portion of the membrane means is curved and also extends outwardly in overlying conforming relationship to the projection, an inner surface of the membrane means sealing against the tip of the projection to define the capillary passage in cooperation with the capillary groove.

11. The apparatus of claim 10, further comprising cover means, secured to the means for defining the fluid flow path, for attaching the membrane means to the means for defining the fluid flow path, said cover means including an aperture through which the projection and the portion of the membrane means extend.

12. The apparatus of claim 11, wherein said portion of the membrane means extending outwardly through the aperture comprises the means for distorting the membrane means, whereby a user applies a force against said portion of the membrane means to deflect the inner surface of the membrane means away from the tip of the projection, thus enlarging the fluid flow path, and causing the flushing flow rate of fluid through the apparatus.

13. The apparatus of claim 12, wherein the means for distorting the membrane means further comprise a flange formed on the means for defining the fluid flow path, whereby the user squeezes the portion of the membrane means toward the flange to deflect the inner portion of the membrane means away from the tip to selectively effect the flushing flow rate of fluid.

14. The apparatus of claim 11, wherein the means for distorting the membrane means comprises a grip that extends from the portion of the membrane means that overlies the tip of the projection, whereby a user grasping the grip pulls on it to deflect the inner surface of the membrane means away from the tip of the projection to enlarge the fluid flow path, in order to selectively cause the flushing flow rate of fluid through the apparatus.

15. Apparatus for controlling fluid flow in a line, comprising:
   (a) a housing including a base and a cover;
   (b) said base having an inlet port and an outlet port connected in fluid communication with an inlet passage and an outlet passage defined in the base;
   (c) a capillary groove formed on a convex curved portion of the base disposed between the inlet passage and the outlet passage, connecting said passages in fluid communication with each other;
   (d) an elastomeric, resilient membrane disposed in overlying relationship to the capillary groove, said membrane being shaped to conform around the convex curved portion of the base, sealing against said portion of the base on each side of the capillary groove so that fluid flows from the inlet passage to the outlet passage through the capillary groove at a greatly restricted flow rate; and
   (e) means associated with the membrane, for enabling a user to selectively deform the membrane away from the capillary groove so that fluid flows from the inlet passage to the outlet passage between the deformed membrane and said portion of the base at a substantially greater flushing flow rate.

16. The apparatus of claim 15, wherein said portion of the base in which the capillary groove is formed comprises a projection that extends outwardly through an aperture formed in the cover, said membrane also extending outwardly through the aperture.

17. The apparatus of claim 16, hwerein the capillary groove is formed in a tip of the projection and the inlet and outlet passages extend through the aperture, defined by an inner surface of the membrane and opposite sides of the projection.

18. The apparatus of claim 16, wherein said means for enabling the user to deform the membrane comprise a portion of the membrane that is exposed, so that a user can selectively effect the flushing flow rate through the apparatus by deflecting said exposed portion of the membrane to one side.

19. The apparatus of claim 18, further comprising guard means projecting outwardly from the cover, adjacent the aperture, for preventing unintended actuation of the flushing flow rate through the apparatus due to the exposed portion of the membrane being deflected by accidental contact with other objects.

20. A method for controlling fluid flow through a fluid line, comprising the steps of:
   (a) defining a fluid flow path between an inlet port and an outlet port adapted for connection to the fluid line, at least a portion of said fluid flow path including a capillary groove that extends across a curved surface and is open along one side;
   (b) sealingly closing the open side of said capillary groove with an elastomeric, resilient membrane that is curved to conform to the curved surface to form a capillary passage;
   (c) restricting fluid flow between the inlet port and the outlet port through the capillary passage to provide a capillary flow rate in the fluid line; and
   (d) selectively distorting the membrane away from the capillary groove, enabling a greater flushing flow rate of fluid through the fluid flow path and in the fluid line, said flushing flow of fluid passing between the membrane and the capillary groove, so as to flush away any obstruction present in the capillary groove.

21. The method of claim 20, further comprising the steps of providing a projection disposed between the inlet port and the outlet port, on a tip of which is formed the curved surface over which extends the capillary groove, and providing a dome-shaped portion on the membrane that overlies the projection and seals against its tip on each side of the capillary groove.

22. The method of claim 20, wherein the step of selectively distorting the membrane comprises the steps of grasping the membrane and pulling on it to deflect it away from the capillary groove.

23. The method of claim 20, wherein the step of selectively distorting the membrane comprises the step of forcing the membrane to one side so that it no longer seals over the capillary groove.

* * * * *

UNITED STATES PATENT AND TRADEMARK OFFICE
CERTIFICATE OF CORRECTION

PATENT NO.  : 4,936,542
DATED       : June 26, 1990
INVENTOR(S) : Beard, Deceased It is certified that error appears in the above-identified patent and that said Letters Patent is hereby corrected as shown below:

| Column | Line | |
|---|---|---|
| 1 | 18 | "ope" should be --open-- |
| 1 | 46 | "retriction" should be --restriction-- |
| 1 | 50 | "not" should be --not-- |
| 3 | 30 | "proxiamte" should be --proximate-- |
| 3 | 54 | "surfce" should be --surface-- |
| 3 | 54 | "inpinges" should be --impinges-- |
| 3 | 55 | "suface" should be --surface-- |
| 3 | 56 | "differnt" should be --different-- |
| 4 | 17 | "fo" should be --of-- |
| 4 | 27 | "inapporpriate" should be --inappropriate-- |
| 5 | 11 | After the word "groove" insert the word --formed-- |
| 7 | 30 | "hwerein" should be --wherein-- |

Signed and Sealed this

Seventh Day of January, 1992

Attest:

HARRY F. MANBECK, JR.

*Attesting Officer*          *Commissioner of Patents and Trademarks*